(12) United States Patent
Noda (10) Patent No.: US 10,311,549 B2
(45) Date of Patent: Jun. 4, 2019

(54) IMAGE PROCESSING APPARATUS, IMAGE PROCESSING METHOD, AND PROGRAM

(71) Applicant: CANON KABUSHIKI KAISHA, Tokyo (JP)

(72) Inventor: Takeshi Noda, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 59 days.

(21) Appl. No.: 14/913,667

(22) PCT Filed: Aug. 1, 2014

(86) PCT No.: PCT/JP2014/070338
§ 371 (c)(1),
(2) Date: Feb. 22, 2016

(87) PCT Pub. No.: WO2015/029695
PCT Pub. Date: Mar. 5, 2015

(65) Prior Publication Data
US 2016/0203588 A1    Jul. 14, 2016

(30) Foreign Application Priority Data
Aug. 27, 2013 (JP) .................................. 2013-175939

(51) Int. Cl.
*A61B 6/00* (2006.01)
*G01T 1/24* (2006.01)
*G06T 5/00* (2006.01)
*H04N 5/32* (2006.01)
(Continued)

(52) U.S. Cl.
CPC ............ *G06T 5/002* (2013.01); *A61B 6/4291* (2013.01); *G01T 1/247* (2013.01); *H04N 5/32* (2013.01); *H04N 5/361* (2013.01); *A61B 6/4233* (2013.01); *G06T 2207/10116* (2013.01)

(58) Field of Classification Search
None
See application file for complete search history.

(56) References Cited

U.S. PATENT DOCUMENTS 5,440,647 A * 8/1995 Floyd, Jr. ................ G06T 5/002
382/132
6,314,160 B1 * 11/2001 Dhawale ................ H04N 5/325
348/E5.088
(Continued)

FOREIGN PATENT DOCUMENTS

JP    2005-052553 A    3/2005
JP    2011-249891 A    12/2011
(Continued)

*Primary Examiner* — Matthew C Bella
*Assistant Examiner* — Jose Torres
(74) *Attorney, Agent, or Firm* — Canon U.S.A., Inc. IP Division (57) ABSTRACT

Even in a case where radiation imaging is performed using a grid, data lack which occurs at a time of radiation detection is appropriately corrected. An FPD controller 105 obtains data of an image captured by detecting radial rays. A data lack ratio calculation unit 111 calculates data lack ratios in the image data. A fitting unit 112 performs fitting so that a model function representing the data lack fits the data lack ratios. A correction processing unit 113 corrects the image data in accordance with the model function obtained by the fitting.

12 Claims, 10 Drawing Sheets

(51) Int. Cl.
*H04N 5/361* (2011.01)
*G06K 9/00* (2006.01)

(56) References Cited

U.S. PATENT DOCUMENTS

| | | | |
|---|---|---|---|
| 6,404,853 B1* | 6/2002 | Odogba | A61B 6/00 250/208.1 |
| 6,944,266 B2* | 9/2005 | Yamazaki | A61B 6/107 378/155 |
| 7,054,474 B1* | 5/2006 | Krieger | G06T 5/002 348/241 |
| 7,156,554 B2* | 1/2007 | Pfister | G06T 5/008 378/154 |
| 10,058,301 B2* | 8/2018 | Tajima | A61B 6/5282 |
| 2003/0016854 A1* | 1/2003 | Inoue | G06T 5/10 382/132 |
| 2004/0096035 A1* | 5/2004 | Yamazaki | A61B 6/107 378/97 |
| 2005/0031182 A1 | 2/2005 | Inoue | |
| 2007/0003125 A1* | 1/2007 | Behiels | G06T 5/10 382/132 |
| 2008/0130823 A1* | 6/2008 | Hagiwara | G06T 11/008 378/4 |
| 2009/0245473 A1* | 10/2009 | Maack | A61B 6/583 378/207 |
| 2011/0033101 A1* | 2/2011 | Foos | G06T 5/005 382/132 |
| 2012/0219203 A1* | 8/2012 | Adachi | A61B 6/585 382/132 |
| 2012/0328073 A1* | 12/2012 | Chiang | A61B 6/032 378/19 |
| 2013/0108021 A1* | 5/2013 | Durst | G01N 23/207 378/71 |
| 2013/0301799 A1* | 11/2013 | Kang | A61B 6/5258 378/62 |
| 2014/0185766 A1* | 7/2014 | Kang | G01T 7/005 378/62 |
| 2014/0219422 A1* | 8/2014 | Nishino | H04N 5/32 378/62 |
| 2015/0131784 A1* | 5/2015 | Tajima | H05G 1/38 378/97 |

FOREIGN PATENT DOCUMENTS

| | | |
|---|---|---|
| JP | 2012-075077 A | 4/2012 |
| JP | 2013-085632 A | 5/2013 |
| JP | 2013-138280 A | 7/2013 |

* cited by examiner

| | | | | |
|---|---|---|---|---|
| G191 | NORMAL | NORMAL | NORMAL | NORMAL |
| G190 | LACK | LACK | LACK | LACK |
| G189 | NORMAL | NORMAL | NORMAL | NORMAL |
| G188 | LACK | LACK | LACK | LACK |
| G187 | NORMAL | NORMAL | NORMAL | NORMAL |
| G186 | LACK | LACK | LACK | LACK |
| G158 | LACK | LACK | LACK | LACK |
| G157 | NORMAL | NORMAL | NORMAL | NORMAL |
| G156 | LACK | LACK | LACK | LACK |
| G155 | NORMAL | NORMAL | NORMAL | NORMAL |
| G154 | NORMAL | NORMAL | NORMAL | NORMAL |

| | | | | | |
|---|---|---|---|---|---|
| G191 | NORMAL | NORMAL | NORMAL | NORMAL | · · · · · |
| G190 | LACK | LACK | LACK | LACK | · · · · · |
| G189 | LACK | LACK | LACK | LACK | · · · · · |
| G188 | LACK | LACK | LACK | LACK | · · · · · |
| G187 | LACK | LACK | LACK | LACK | · · · · · |
| G186 | LACK | LACK | LACK | LACK | · · · · · |
| G158 | LACK | LACK | LACK | LACK | · · · · · |
| G157 | LACK | LACK | LACK | LACK | · · · · · |
| G156 | LACK | LACK | LACK | LACK | · · · · · |
| G155 | NORMAL | NORMAL | NORMAL | NORMAL | · · · · · |
| G154 | NORMAL | NORMAL | NORMAL | NORMAL | · · · · · |

FIG. 11

IMAGE PROCESSING APPARATUS, IMAGE PROCESSING METHOD, AND PROGRAM

TECHNICAL FIELD

The present invention relates to a technique of correcting data of an image captured by detecting radial rays.

BACKGROUND ART

In recent years, a flat panel detector (FPD) which includes fluorescent substances disposed on a TFT active matrix substrate, which accumulates X-rays as charge, and which provides X-ray image data by converting the charge into digital signals has been in practical use and frequently used. Such an X-ray imaging apparatus is integrally formed with general modality and configured as a dedicated apparatus. However, there is a demand for replacing an imaging medium, such as a film and an imaging plate, of existing modality by the FPD.

In a case where the imaging medium of the existing modality is replaced by the FPD, construction of an interface between an X-ray generation apparatus and the FPD may be difficult. To address this problem, PTL 1 discloses a technique of starting an operation of accumulating charges by detecting irradiation with X-rays on an FPD side without an interface between an X-ray generation apparatus and an FPD.

Here, although the FPD converts photons into electrons by photodiodes, dark charge is generated due to thermal excitation or leakage current even in a case where photons do not exist in practice. When the dark charge is accumulated, the dark charge is added to charge generated by X-rays actually emitted, and therefore, non-uniformity of data is generated resulting in generation of artifact. Furthermore, since the dark charge is accumulated, an amount of the accumulated X-rays is reduced. Therefore, the FPD performs a resetting operation so that the dark charge is discharged while TFTs are constantly in an on state before X-ray imaging is performed.

However, in a case where the operation of accumulating charge by detecting irradiation with X-rays as described above is started, a certain amount of X-rays is required before the charge accumulation operation is started, and the resetting operation is performed before the charge accumulation operation is started. Therefore, the charge generated by the X-rays emitted before the charge accumulation operation is started is discharged, and accordingly, data lack occurs resulting in generation of artifact.

On the other hand, PTL 2 discloses a technique of a resetting operation performed for each line at a time of detection of X-rays while an even-numbered line and an odd numbered line are replaced by each other for each frame. In the technique disclosed in PTL 2, artifact is generated every other line due to data lack in a period of time from when irradiation with X-rays is performed to when a charge accumulation operation is started, and therefore, the artifact may be corrected by an interpolation process.

Here, in X-ray imaging, imaging using a grid is frequently performed. The grid which is one of basic tools to be used in X-ray imaging shields X-rays scattered in an inside of a subject so that a blur of X-ray image data is suppressed. In imaging using a grid, in the technique disclosed in PTL 2, in a case where a direction of grid lines and a direction of scanning lines match each other, grid stripes and artifact generated at a time of X-ray detection interfere with each other. If the X-ray image data is corrected by the interpolation process, artifact may be additionally generated or the grid stripes may be partially removed.

PTL 3 discloses a technique of removing grid stripes by model fitting. However, artifact generated at a time of X-ray detection is not taken into consideration in the technique disclosed in PTL 3, and therefore, the grid stripes may not be appropriately removed in a case where the grid stripes are partially removed.

CITATION LIST

Patent Literature

PTL 1: Japanese Patent Laid-Open No. 2012-075077
PTL 2: Japanese Patent Laid-Open No. 2011-249891
PTL 3: Japanese Patent Laid-Open No. 2005-52553

SUMMARY OF INVENTION

Technical Problem

However, artifact may be generated depending on a direction in which the grid is set in the related art. Therefore, if imaging is required to be performed again, a patient is unnecessarily exposed to radiation.

Accordingly, an object of the present invention is to appropriately correct data lack in image data generated at a time of radiation detection even in a case where radiation imaging is performed using a grid.

Solution to Problem

An image processing apparatus according to the present invention includes obtaining means for obtaining data of an image captured by detecting radial rays, calculating means for calculating data lack ratios of the image data, fitting means for fitting a model function representing data lack to the data lack ratios, and correcting means for correcting the data lack of the image data in accordance with the model function subjected to the fitting performed by the fitting means.

Advantageous Effects of Invention

According to the present invention, data lack in image data which occurs at a time of radiation detection may be appropriately corrected even in a case where radiation imaging is performed using a grid.

DESCRIPTION OF EMBODIMENTS

Embodiments of the preset invention will be described in detail hereinafter with reference to the accompanying drawings.

A first embodiment of the present invention will now be described. Although a sensor employing PIN photodiodes is used in an X-ray imaging apparatus serving as a radiation imaging apparatus of this embodiment, a sensor employing MIS photodiodes may be used. Alternatively, a direct FPD which directly converts X-rays into electrons may be used.

Figure 1:
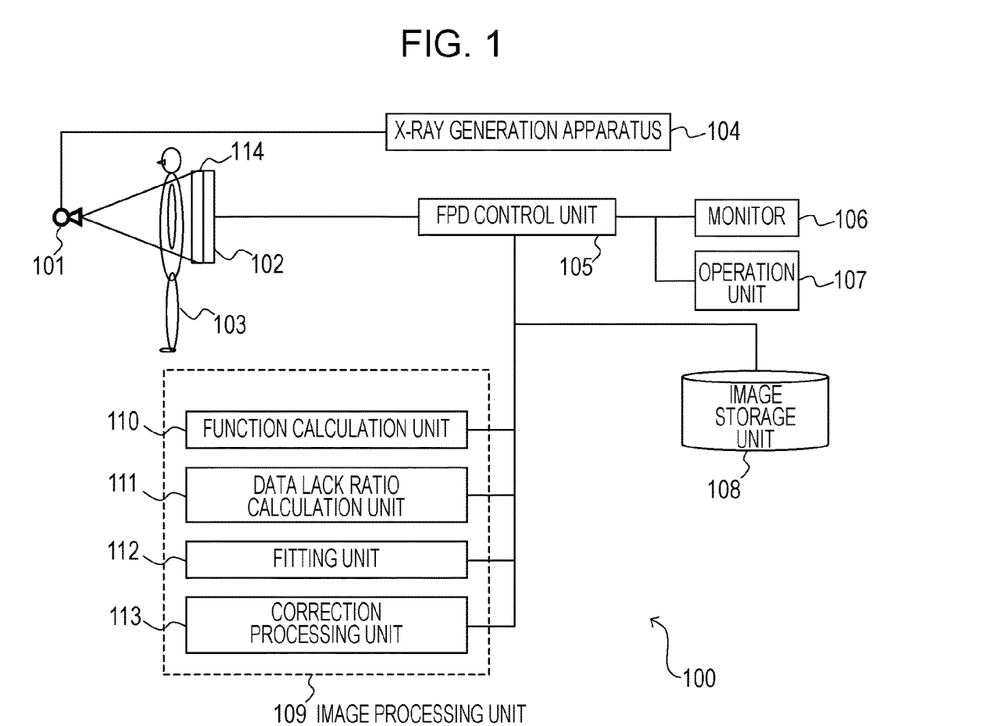
FIG. 1 is a diagram illustrating a configuration of an X-ray imaging apparatus according to embodiments of the present invention.

FIG. 1 is a diagram illustrating a configuration of an X-ray imaging apparatus 100 according to a first embodiment of the present invention. In FIG. 1, an X-ray tube 101 irradiates a subject 103 with X-rays. An X-ray generation apparatus 104 applies a high-voltage pulse to the X-ray tube 101 when an exposure switch is pressed so that X-rays are generated. An FPD 102 converts X-rays supplied through the subject 103 into visible light by fluorescent substances and detects electric signals by photodiodes under control of the FPD controller 105. The detected electric signals are subjected to AD conversion so that digital signals are obtained and output to an FPD controller 105 as X-ray image data. A grid 114 disposed in front of the FPD 102 shields X-rays scattered in an inside of the subject so as to suppress a blur of the X-ray image data.

The FPD controller 105 is connected to an image processing unit 109, an image storage unit 108, a monitor 106, and an operation unit 107. Furthermore, the FPD controller 105 incorporates at least one computer. The computer includes a main controller, such as a CPU, and a storage unit including a read only memory (ROM) and a random access memory (RAM), for example. The computer further includes a graphic controller, such as a graphics processing unit (GPU), a communication unit, such as a network card, and an input/output unit, such as a keyboard, a display, or a touch panel. Note that these components are connected to one another through a bus or the like and controlled when the main controller executes a program stored in the storage unit.

The monitor 106 displays the X-ray image data supplied from the FPD controller 105. The operation unit 107 inputs an instruction to the image processing unit 109 or the FPD 102. The image storage unit 108 stores the X-ray image data output from the FPD controller 105 and X-ray image data processed by the image processing unit 109.

The image processing unit 109 including a function calculation unit 110, a data lack ratio calculation unit 111, a fitting unit 112, and a correction processing unit 113 processes the obtained X-ray image data in accordance with an instruction issued by the FPD controller 105.

The function calculation unit 110 calculates a model function representing a shape of artifact generated due to data lack caused by the resetting operation in a period of time from when the FPD 102 detects irradiation with X-rays to when the operation of accumulating charge is started. The data lack ratio calculation unit 111 calculates a data lack ratio by calculating a ratio of the number of pixels in which data lack is generated to the number of pixels in which data lack is not generated. The fitting unit 112 performs fitting so that a model function generated by the function calculation unit 110 fits data lack ratios calculated by the data lack ratio calculation unit 111. The correction processing unit 113 performs a process of correcting the X-ray image data using the model function obtained by the fitting performed by the fitting unit 112.

Next, a process performed by the X-ray imaging apparatus 100 of this embodiment will be described with reference to FIG. 2. In step S101, the FPD controller 105 obtains X-ray image data. This process is performed such that the X-ray generation apparatus 104 applies a high-voltage pulse to the X-ray tube 101 and irradiates the subject with X-rays. Although an arbitrary value may be set as a condition for imaging X-ray image data, a value of approximately 100 kV and a value of approximately 2 mAs are set in imaging of a breast portion or the like. Furthermore, a distance between the FPD 102 and the X-ray tube 101 is set to approximately 100 cm to approximately 150 cm in general. In this embodiment, any interface is not provided between the X-ray generation apparatus 104 and the FPD 102, and the FPD 102 starts the operation of accumulating charge by detecting the irradiation with X-rays.

Figure 3:
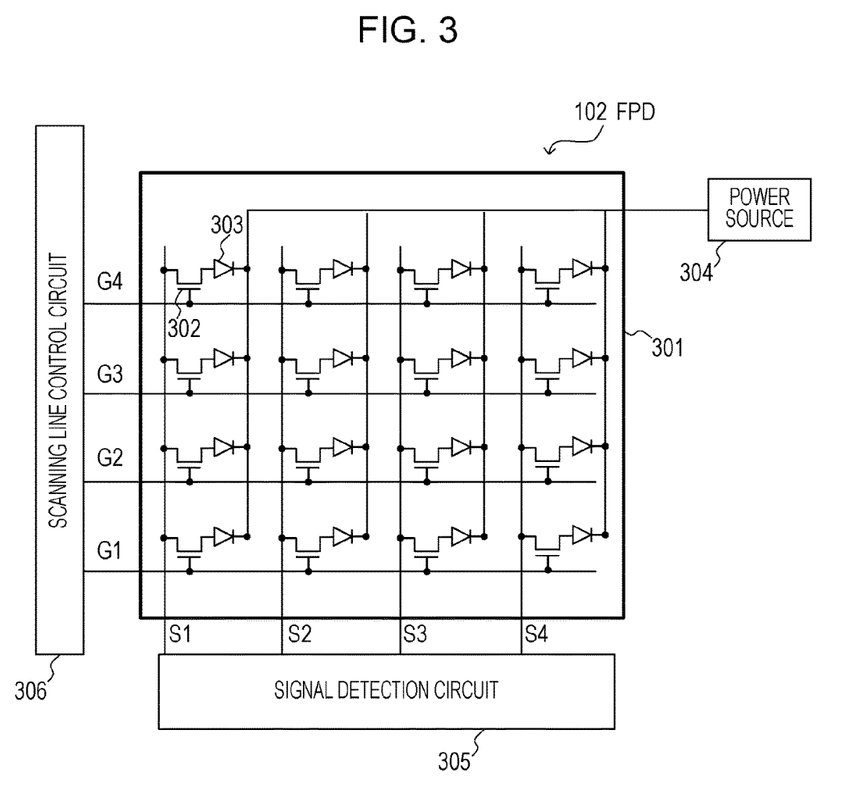
FIG. 3 is a diagram illustrating a circuit configuration of an FPD.

A circuit configuration of the FPD 102 will now be described with reference to FIG. 3. The FPD 102 forms one pixel by a combination of a TFT 302 and a photodiode 303 on a glass substrate 301. It is assumed here that the FPD 102 includes one million pixels in a matrix of 1000 pixels by 1000 pixels. Note that only 16 pixels in the million pixels are illustrated for the purpose of illustration in FIG. 3. Note that the FPD 102 has a configuration of an example of a radiation detection apparatus.

A scanning line control circuit 306 successively applies an on-signal to G1 to G1000 (not illustrated after G5 onwards) so as to turn on switches of the TFTs 302. By this, charges may be read from the photodiodes 303 on a line by line basis. Signal lines S1 to S1000 (not illustrated after the line S5 onwards) transmit charges read from the photodiodes 303, and the charges are read by a signal detection circuit 305. The signal detection circuit 305 executes holding, amplifying, AD conversion, and the like on the read charges and outputs the processed charges to the FPD controller 105 as digital signals. A power source 304 supplies an operation voltage to the photodiodes 303.

Figure 4:
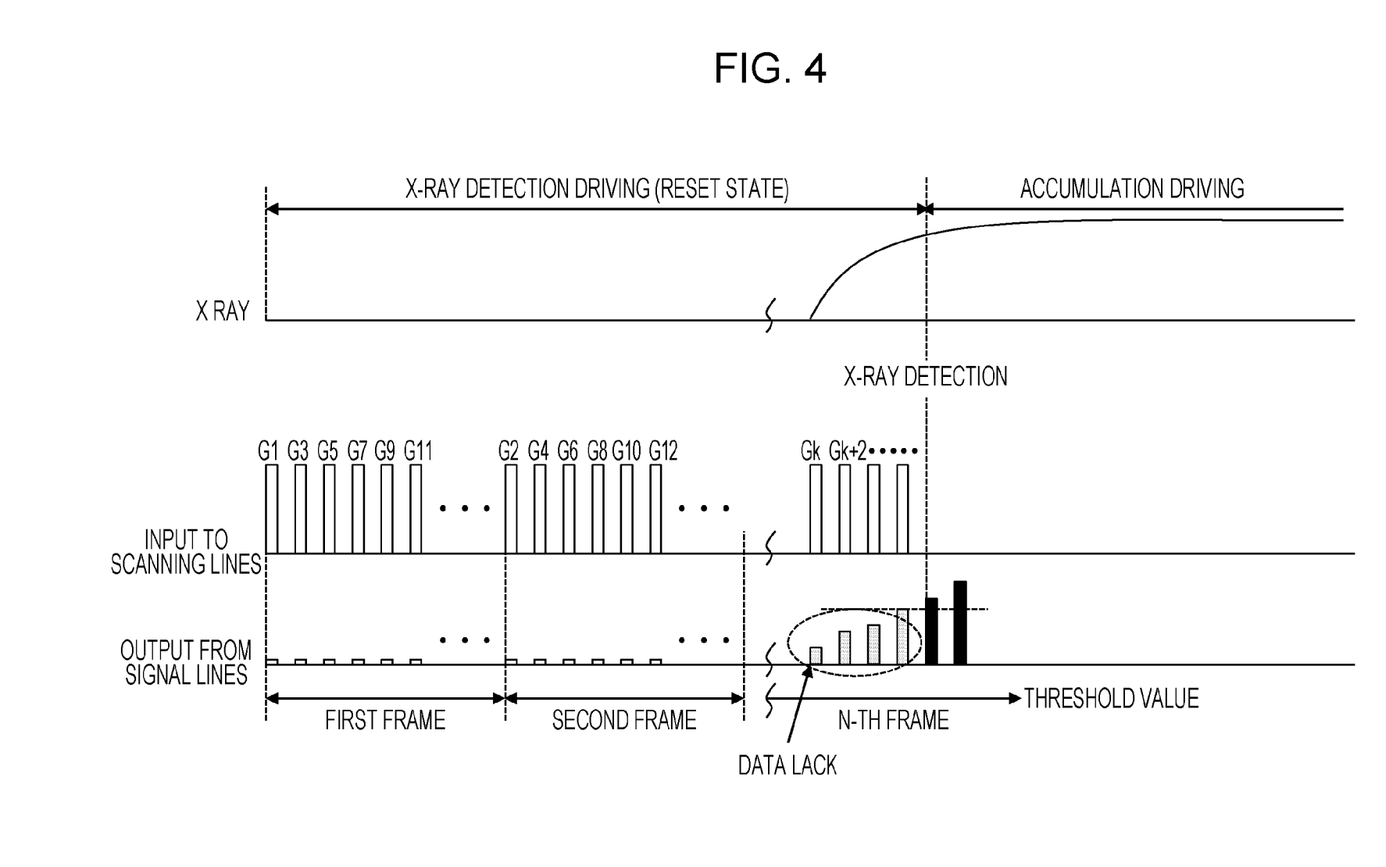
FIG. 4 is a timing chart illustrating driving of the FPD according to a first embodiment.

FIG. 4 is a timing chart illustrating driving of the FPD 102. In FIG. 4, the FPD 102 waits in a state referred to as an "X-ray detection driving" state when irradiation with X-rays is not performed. In the "X-ray detection driving" state, the scanning line control circuit 306 successively drives odd-numbered lines, that is, the scanning lines G1, G3, G5, and so on with a line interval of one line (a line interval of at least one line) in a first frame, and reads dark charge of pixels connected to the odd-numbered scanning lines so as to reset the odd-numbered scanning lines. Subsequently, the scanning line control circuit 306 successively drives even-numbered lines, that is, the scanning lines G2, G4, G6, and so on with a line interval of one line (a line interval of at least one line) in a second frame, and reads pixels connected to the even-numbered scanning lines so as to reset the even-numbered scanning lines. In this way, the odd-numbered lines are reset in odd-numbered frames whereas the even-numbered lines are reset in even-numbered frames in this embodiment.

When X-rays are emitted, charges are generated by the photodiodes 303, and accordingly, output of the signal lines is increased. The signal detection circuit 305 detects the irradiation with X-rays when output of a signal line exceeds a predetermined threshold value. When the irradiation with X-rays is detected by the signal detection circuit 305, the scanning line control circuit 306 turns all the TFTs 302 off. By this, the operation of accumulating charge is started. Although as the threshold value is smaller, detection of X-rays is faster, malfunction, such as noise, occurs. Accordingly, an appropriate value corresponding to the detection sensitivity and a noise level is set.

In the X-ray detection operation described above, a time lag is generated between start of the X-ray irradiation and the X-ray detection. Since charges corresponding to X-rays emitted before the charge accumulation operation is performed are discharged by the resetting operation, the charges may not contribute the X-ray image data, and accordingly, artifact is generated due to data lack.

Figure 5:
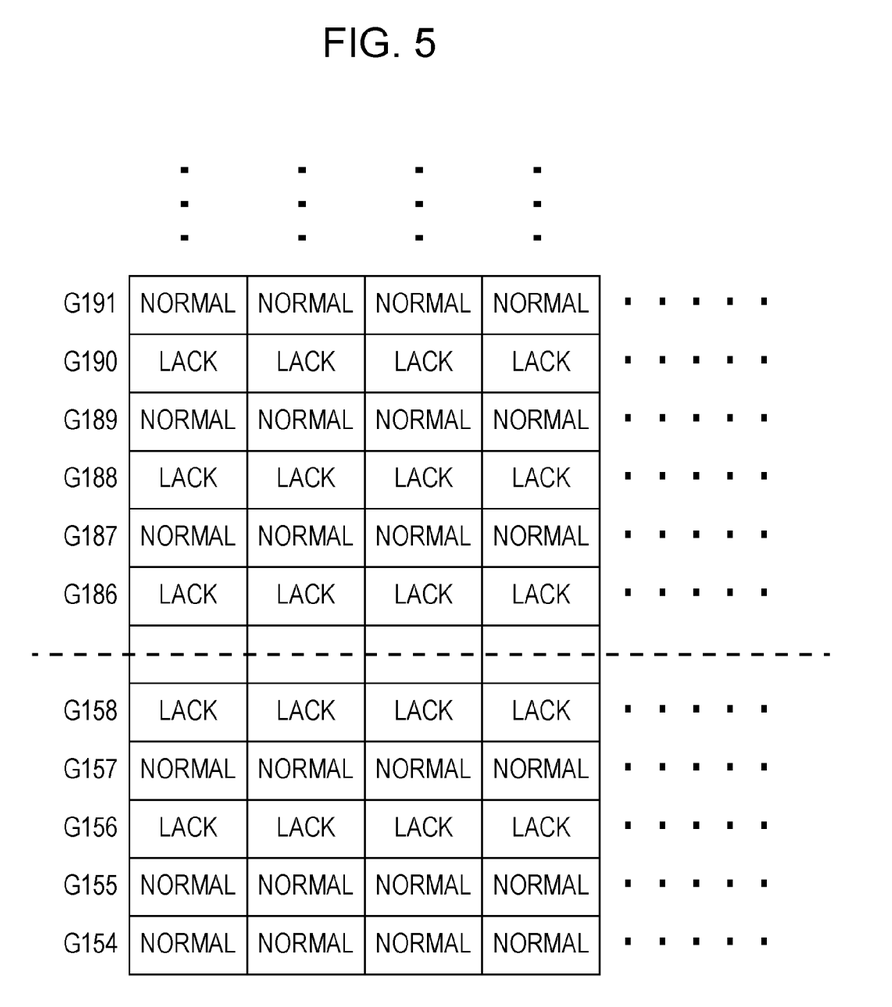
FIG. 5 is a diagram illustrating X-ray image data obtained in the first embodiment.

In step S102, the data lack ratio calculation unit 111 calculates data lack ratios using the X-ray image data obtained in step S101. FIG. 5 is a diagram illustrating the X-ray image data obtained in step S101. Here, one rectangle corresponds to one pixel in FIG. 5. It is assumed that X-ray irradiation is started on a line G156 of an even-numbered frame and an X-ray is detected in a line G190. In this case, since the odd-numbered lines are not reset, charges of normal pixel values are accumulated. On the other hand, charges to be accumulated by the X-ray irradiation in the even-numbered lines G156 to G190 are lacked due to the resetting operation.

Since pixel values of natural image data are continuously changed in general, pixel values in adjacent lines are close to each other in a case where a high-frequency component, such as an edge or a grid, is not included in a subject. Accordingly, in this embodiment, as represented by Expression 1 below, data lack ratios $A_T(x, y)$ are calculated by calculating ratios of pixels in which data lack occurs in lines to pixels in which data lack does not occur taking the fact that adjacent lines (adjacent lines in a y direction) are normal into consideration. Here, P(x, y) represents a pixel value in a position coordinate (x, y).

[Math. 1]

$$A_T(x, y) = 1 - \frac{P(x, y)}{P(x, y+1)}$$ Expression 1

In step S103, the fitting unit 112 fits the model function calculated by the function calculation unit 110 to the data lacking ratios calculated in step S102. By this, true data lack ratios are calculated by removing a high-frequency component of an edge or a grid from the data lacking ratios calculated in step S102.

The model-function fitting process will now be described in detail. In a period of time from start of X-ray irradiation to detection of X-rays, data lack occurs since charges accumulated in a period of time from the start of X-ray irradiation to reset of a certain line are lacked. Accordingly, the data lack is obtained by perform time integration on an X-ray waveform obtained in the period of time from the start of X-ray irradiation to the reset of the certain line.

The X-ray waveform may be the same as a shape of a voltage pulse of the X-ray generation apparatus 104. A general voltage pulse rises while having rounding caused by an electric impedance. A model of this waveform is represented by Expression 2.

[Math. 2]

$$V_{OUT} = V\left(1 - e^{-\frac{t-t_0}{\tau}}\right)$$ Expression 2

Figure 6:
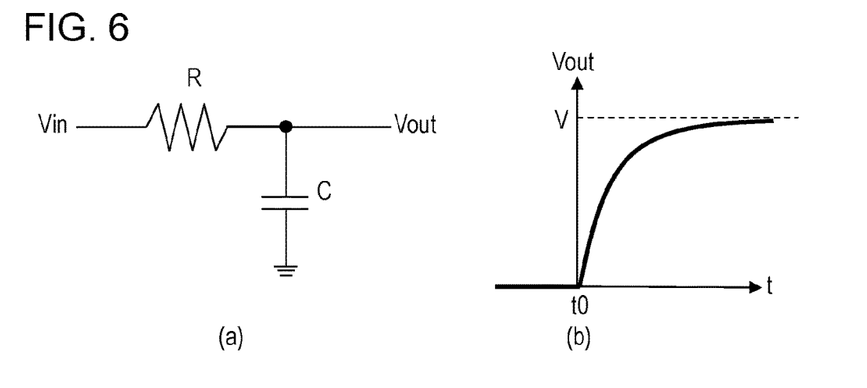
FIG. 6 includes diagrams illustrating an X-ray waveform model.

As represented by Expression 2, rise of the voltage pulse may be represented by a time constant $\tau$ which is an integral of a resistance R and a capacitance C illustrated in FIG. 6(a) and has a waveform illustrated in FIG. 6(b). Accordingly, the data lack may be represented by a model function represented by Expression 3 below in which integration is performed from an X-ray irradiation start time t0 to a reset time t of the certain line.

[Math. 3]

$$A(t, t_0, \tau, V) = \int_{t_0}^{t} V\left(1 - e^{-\frac{\xi-t_0}{\tau}}\right)d\xi = V(t-t_0) + V\tau\left(e^{-\frac{t-t_0}{\tau}} - 1\right)$$ Expression 3

Note that "$\tau$", "V", and "$t_0$" in Expression 3 are unknown numbers determined depending on a designed value and a generation condition of the X-ray generation apparatus 104 and obtained by fitting. Specifically, "$\tau$", "V", and "$t_0$" are obtained such that Expression 4 below is minimized. The Newton's method or the conjugate gradient method which are generally used may be used as a minimization algorithm.

[Math. 4]

$$s = (A_T(x, y(t)) - A(t, t_0, \tau, V))^2$$ Expression 4

Figure 7:
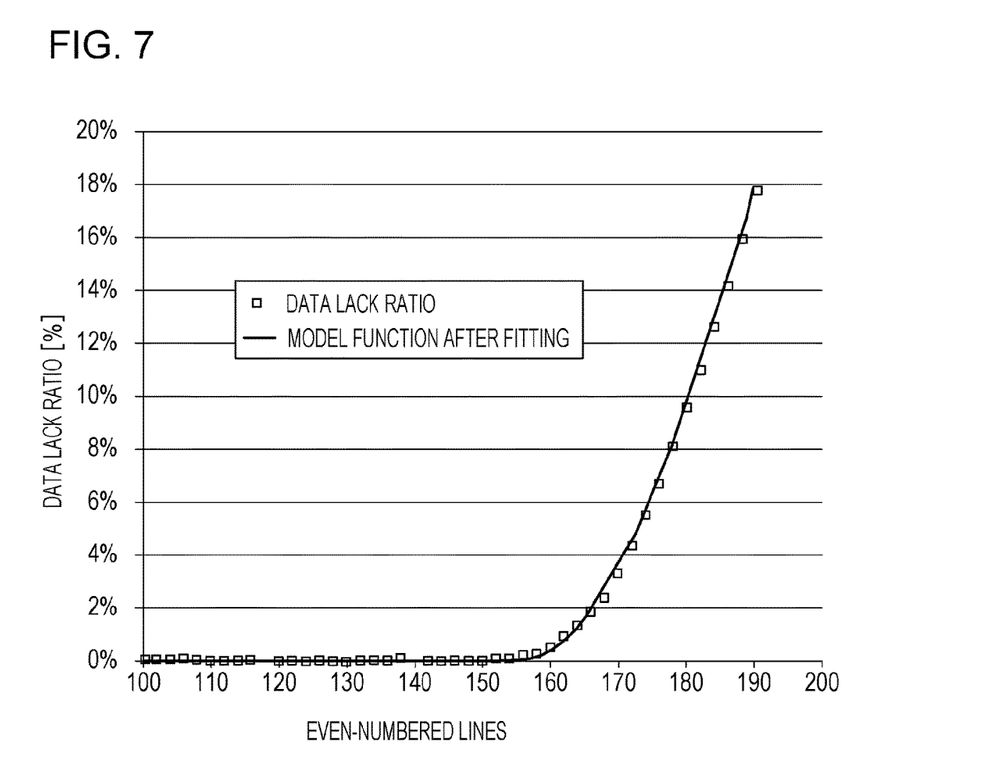
FIG. 7 is a diagram illustrating data lack ratios calculated from the X-ray image data captured in a state in which a subject does not actually exist and a model function (a solid line) obtained by fitting using the data lack ratios.

FIG. 7 is a diagram illustrating data lack ratios (□) calculated from X-ray image data captured in a state in which a subject does not actually exist and a model function (a solid line) obtained by fitting using the data lack ratios. As illustrated in FIG. 7, the model function obtained by the fitting well fits the data lack ratios calculated from the X-ray image data.

Figure 8:
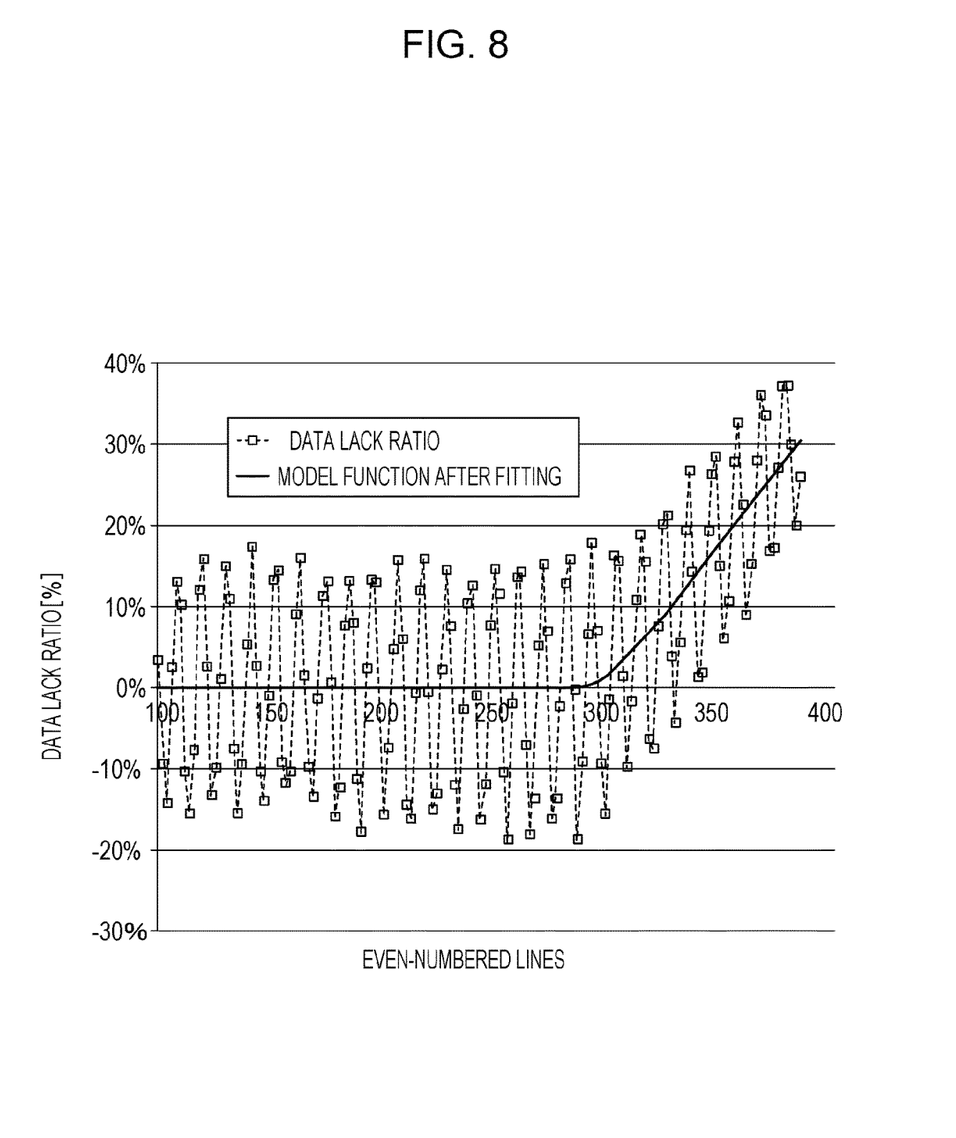
FIG. 8 is a diagram illustrating data lack ratios calculated from X-ray image data captured after a grid having a periodic structure similar to a Nyquist frequency of an FPD is inserted.

FIG. 8 is a diagram illustrating the data lack ratios (a dotted line and □) calculated from X-ray image data captured after the grid 114 having a periodic structure similar to a Nyquist frequency of the FPD 102 is inserted. In this example, the X-ray image data is obtained in a state in which the grid 114 is inserted such that grid lines are in parallel to the scanning lines. As illustrated in FIG. 8, the data lack ratios calculated from the X-ray image data obtained in the state in which the grid 114 is inserted such that the grid lines are in parallel to the scanning lines have "beat" added to the data lack ratios illustrated in FIG. 7.

The model function obtained by the fitting has a shape of data lack ratios based on the X-ray waveform and driving of the FPD 102. Accordingly, the model function obtained by fitting is not affected by stripes of the grid or the "beat" inserted into the data lack ratios calculated from the X-ray image data, and true data lack ratios based on the X-ray waveform and the driving of the FPD 102 may be extracted.

In step S104, the correction processing unit 113 corrects the X-ray image data using the model function obtained by the fitting. The correction processing unit 113 corrects data lack of the X-ray image data which occurs in a period of time from start of X-ray irradiation to start of the charge accumulation operation using the model function obtained by the fitting. This correction process is performed in accordance with Expression 5 below while it is assumed that a pixel value after the correction is denoted by "$P_c(x, y)$" and a pixel value before the correction is denoted by "$P(x, Y)$".

[Math. 5]

$$P_C(x, y) = \frac{P(x, y)}{1 - A(t(y), t_0, \tau, V)} \qquad \text{Expression 5}$$

Consequently, even in a case where the grid lines extend in parallel to the scanning lines of the FPD 102, data lack which occurs in the period of time from the start of X-ray irradiation to the start of the charge accumulation operation is appropriately corrected so that the X-ray image data is restored. That is, even in a case where radiation imaging is performed using a grid, the correction processing unit 113 may appropriately correct data lack in X-ray image data which occurs at a time of radiation detection.

Next, a second embodiment of the present invention will be described. Note that an X-ray imaging apparatus according to the second embodiment has a configuration which is the same as that illustrated in FIG. 1, and therefore, reference numerals the same as those illustrated in FIG. 1 are used in a description below.

In the first embodiment, driving for switching between resetting in the even-numbered lines and resetting in the odd-numbered lines is performed for each frame during the "X-ray detection driving". However, data lack which occurs in a period of time from start of X-ray irradiation to detection of X-rays may be corrected without such special driving.

Figure 2:
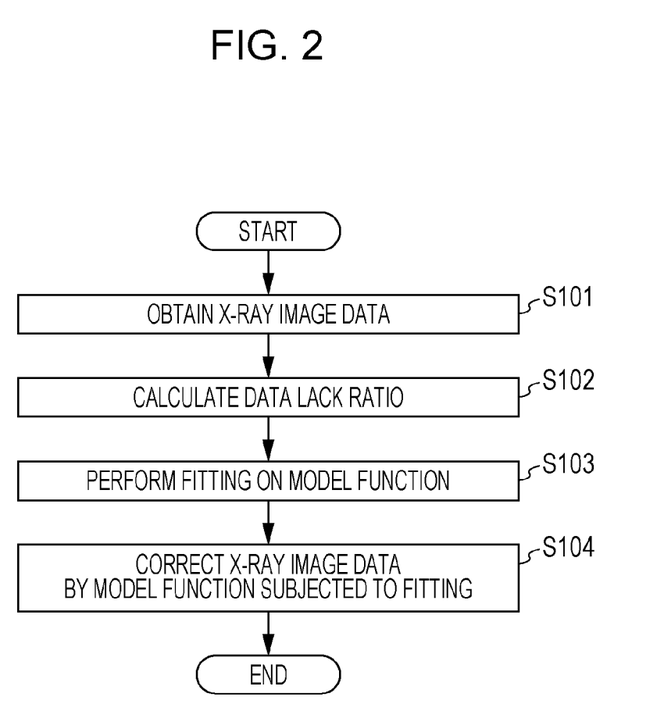
FIG. 2 is a flowchart illustrating a process performed by the X-ray imaging apparatus according to the embodiments of the present invention.
Figure 9:
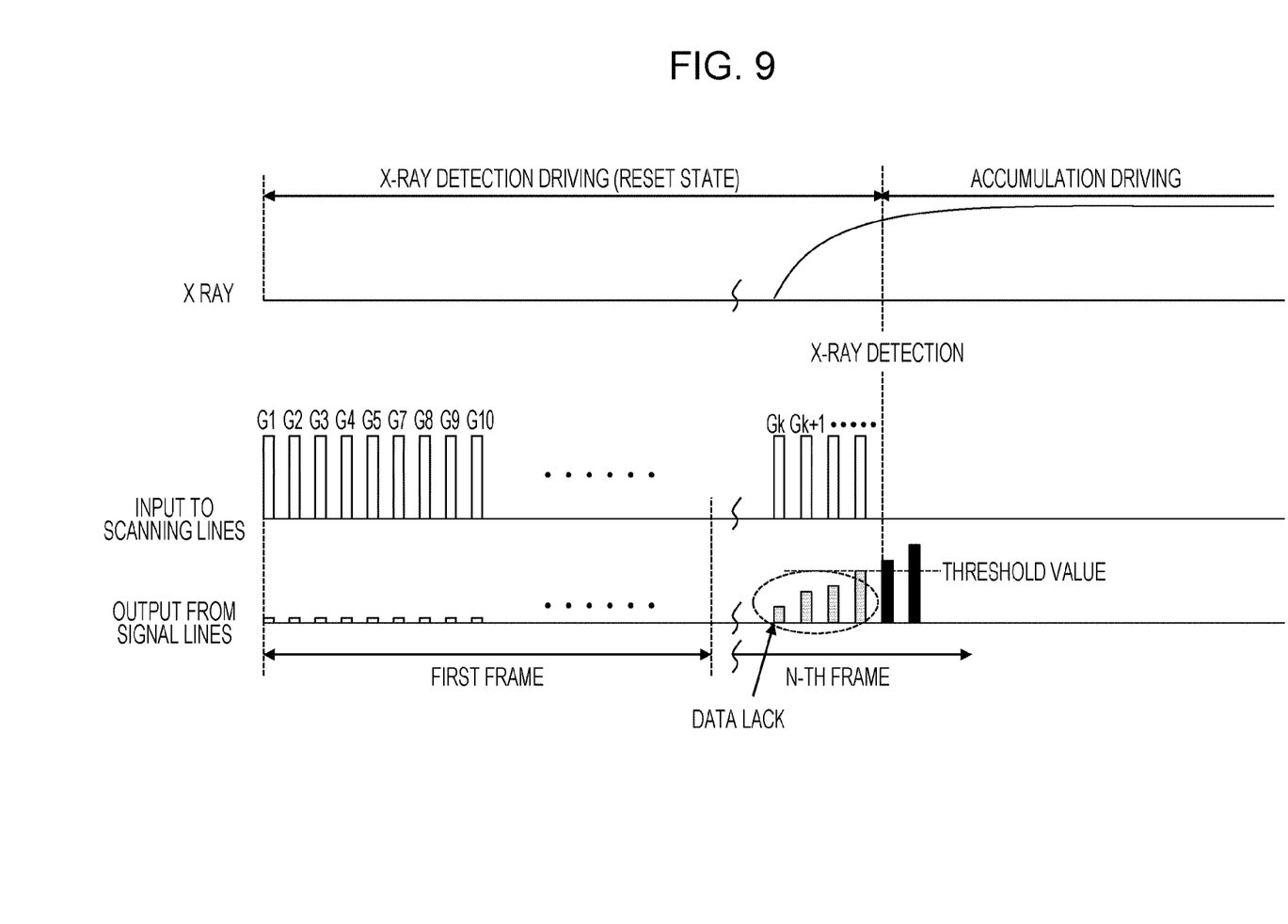
FIG. 9 is a timing chart illustrating driving of an FPD according to a second embodiment.
Figure 10:
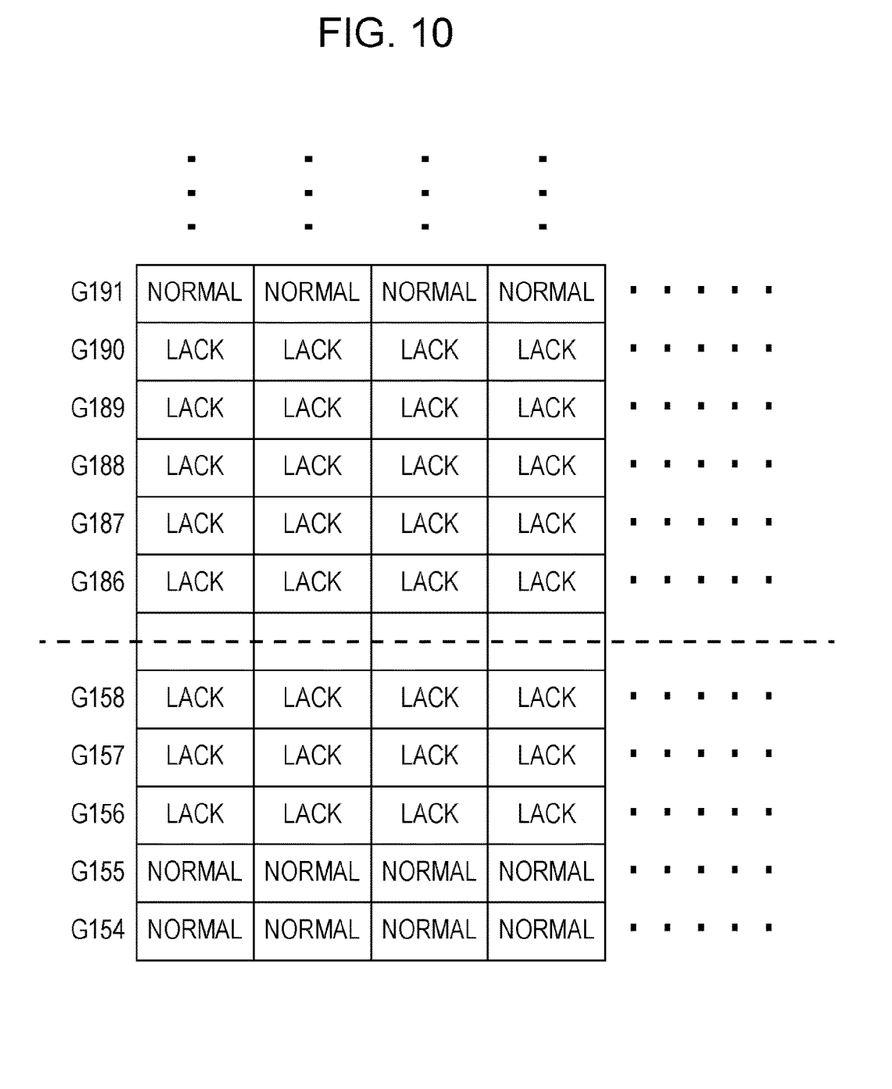
FIG. 10 is a diagram illustrating X-ray image data obtained in the second embodiment.

As with step S101 of FIG. 2, an FPD controller 105 obtains X-ray image data. FIG. 9 is a timing chart illustrating driving of an FPD 102 according to the second embodiment. In the driving of the FPD 102 according to the second embodiment, a resetting operation is successively performed on lines G1 to G4 and so on in an "X-ray detection driving" state, and all scanning lines are reset in one frame. Accordingly, data lack continuously occurs in the second embodiment as illustrated in FIG. 10.

A data lack ratio calculation unit 111 calculates data lack ratios $A_T$ from the X-ray image data obtained by the FPD controller 105 in accordance with Expression 6 below.

[Math. 6]

$$A_T(x, y) = 1 - \frac{P(x, y)}{P(x, y_{detect} + 1)} \qquad \text{Expression 6}$$

In Expression 6, "$y_{detect}$" denotes a line in which an X-ray is detected. Specifically, a charge accumulation operation is normally started in a line $y_{detect}+1$ which is positioned immediately on the line $y_{detect}$, and accordingly, data lack ratios are calculated using the line $y_{detect}+1$ as a reference.

Figure 11:
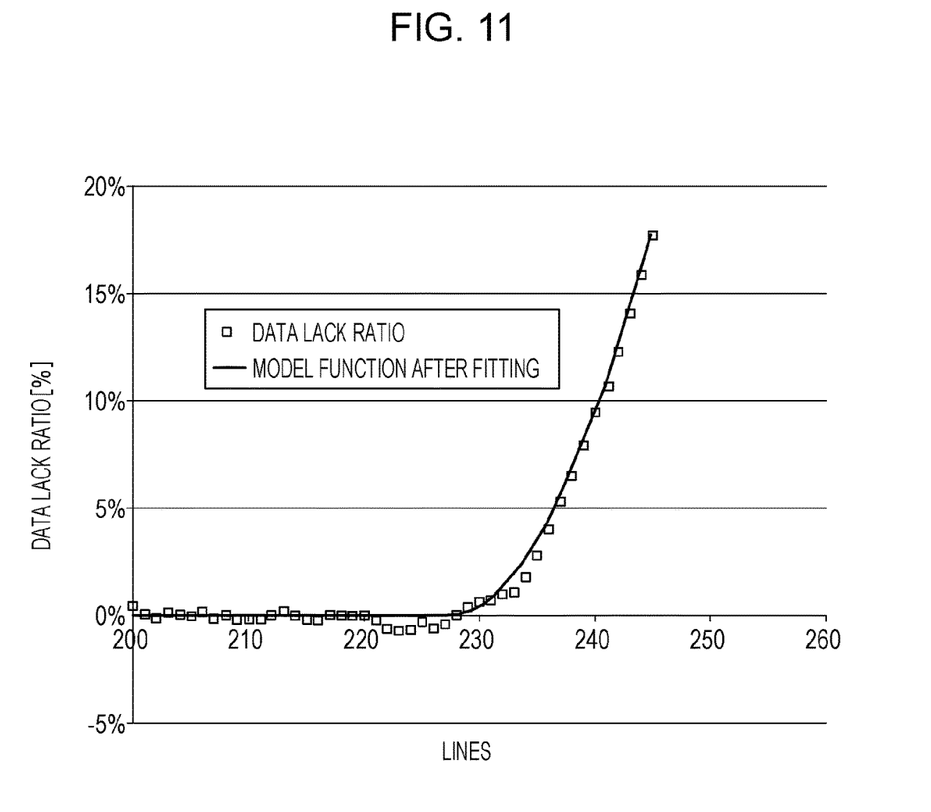
FIG. 11 is a diagram illustrating data lack ratios calculated by a data lack ratio calculation unit and a model function obtained by fitting using the data lack ratios according to the second embodiment.

FIG. 11 is a diagram illustrating data lack ratios $A_T(\square)$ calculated by a data lack ratio calculation unit 111 and a model function (a solid line) obtained by fitting using the data lack ratios according to the second embodiment. The data lack ratios $A_T$ vary due to influence of a subject. A fitting unit 112 performs fitting so that a model function of Expression 3 fits the data lack ratios $A_T$. The model function represented by Expression 3 has a shape of the data lack ratios based on an X-ray waveform and driving of the FPD 102. Accordingly, the model function obtained by the fitting is not affected by the subject included in the data lack ratios calculated from the X-ray image data, and true data lack ratios based on the X-ray waveform and the driving of the FPD 102 may be extracted.

The correction processing unit 113 corrects the X-ray image data using the model function (a model coefficient obtained by the fitting) in which a coefficient is fixed by the fitting). The correction processing unit 113 corrects data lack of the X-ray image data which occurs in a period of time from start of X-ray irradiation to start of a charge accumulation operation using the model function (the model coefficient obtained by the fitting) represented by Expression 3 in which the coefficient is fixed by the fitting. This correction is performed in accordance with Expression 7 below while it is assumed that a pixel value after the correction is denoted by "$P_c(x, y)$" and a pixel value before the correction is denoted by "$P(x, y)$".

[Math. 7]

$$P_C(x, y) = \frac{P(x, y)}{1 - A(t(y), t_0, \tau, V)} \qquad \text{Expression 7}$$

Consequently, even in a case where lines are continuously reset by driving of an FPD, data lack which occurs in a period of time from start of X-ray irradiation to start of a charge accumulation operation is appropriately corrected so that X-ray image data is restored. That is, even in a case where radiation imaging is performed using a grid, the correction processing unit 113 may appropriately correct data lack in X-ray image data generated at a time of radiation detection.

Furthermore, the present invention is realized by executing the following process. Specifically, software (a program) which realizes the functions of the foregoing embodiments is supplied to a system or an apparatus through a network or various storage media, and a computer (or a CPU or an MPU) included in the system or the apparatus reads and executes the program.

The invention is not limited to the disclosed exemplary embodiments, and various modifications and changes may be made without departing from the spirit and the scope of the present invention. Accordingly, the claims are attached below to disclose a range of the present invention.

This application claims the benefit of Japanese Patent Application No. 2013-175939 filed Aug. 27, 2013, which is hereby incorporated by reference herein in its entirety.

REFERENCE SIGNS LIST

100 X-RAY IMAGING APPARATUS
101 X-RAY TUBE
102 FPD
103 SUBJECT
104 X-RAY GENERATION APPARATUS
105 FPD CONTROLLER
106 MONITOR
107 OPERATION UNIT

108 IMAGE STORAGE UNIT
109 IMAGE PROCESSING UNIT
110 FUNCTION CALCULATION UNIT
111 DATA LACK RATIO CALCULATION UNIT
112 FITTING UNIT
113 CORRECTION PROCESSING UNIT
114 GRID

The invention claimed is:

1. An image processing apparatus comprising:
a CPU; and
at least one memory, the CPU and the at least one memory cooperating to provide:
an obtaining unit configured to obtain image data captured by detecting radial rays via a grid disposed in front of a radiation detector while resetting odd-numbered lines or even-numbered lines of the radiation detector;
a calculating unit configured to calculate data lack information of the image data including grid components caused by the grid from a start of radial rays by an irradiating unit to detection of the radial rays by the obtaining unit, by calculating ratios of pixels in which data lack occurs in odd-numbered lines or even-numbered lines to pixels in which data lack does not occur using adjacent lines that are normal, wherein the data lack occurs in odd-numbered lines or even-numbered lines by resetting the odd-numbered lines or the even-numbered lines of the radiation detector;
a fitting unit configured to fit a model function representing data lack to the data lack information; and
a correcting unit configured to correct the image data using data lack information obtained by reducing grid components in accordance with the model function subjected to the fitting performed by the fitting unit.

2. The image processing apparatus according to claim 1, wherein the model function is obtained by performing time integration on a certain X-ray waveform.

3. The image processing apparatus according to claim 2, wherein the calculating unit calculates the data lack information in accordance with ratios of pixels in which data lack occurs to pixels in which data lack does not occur in the image data.

4. The image processing apparatus according to claim 3, wherein the image data is based on charges read with an interval of at least one line or without a line interval in a radiation detection apparatus including a plurality of lines including pixels which convert the radial rays into the charges.

5. The image processing apparatus according to claim 2, wherein the image data is based on charges read with an interval of at least one line or without a line interval in a radiation detection apparatus including a plurality of lines including pixels which convert the radial rays into the charges.

6. The image processing apparatus according to claim 1, wherein the calculating unit calculates the data lack information in accordance with ratios of pixels in which data lack occurs to pixels in which data lack does not occur in the image data.

7. The image processing apparatus according to claim 6, wherein the image data is based on charges read with an interval of at least one line or without a line interval in a radiation detection apparatus including a plurality of lines including pixels which convert the radial rays into the charges.

8. The image processing apparatus according to claim 1, wherein the image data is based on charges read with an interval of at least one line or without a line interval in a radiation detection apparatus including a plurality of lines including pixels which convert the radial rays into the charges.

9. The image processing apparatus according to claim 1, wherein the wherein the grid is disposed such that grid lines of the grid are in parallel to scanning lines of a radiologic imaging apparatus.

10. The image processing apparatus according to claim 1, wherein the data lack information calculated from the image data captured via the grid has a beat.

11. An image processing method executed by an image processing apparatus, the image processing method comprising:
an obtaining step of using an obtaining device to obtain image data captured by detecting radial rays via a grid disposed in front of a radiation detector while resetting odd-numbered lines or even-numbered lines of the radiation detector;
a calculating step of calculating data lack information of the image data including grid components caused by the grid from a start of a radial rays to detection of the radial rays by the obtaining device, by calculating ratios of pixels in which data lack occurs in odd-numbered lines or even-numbered lines to pixels in which data lack does not occur using adjacent lines that are normal, wherein the data lack occurs in odd-numbered lines or even-numbered lines by resetting the odd-numbered lines or the even-numbered lines of the radiation detector;
a fitting step of fitting a model function representing data lack to the data lack information; and
a correcting step of correcting the image data using data lack information obtained by reducing grid components in accordance with the model function subjected to the fitting performed in the fitting step.

12. A non-transitory computer-readable storage medium storing a program that causes a computer to execute:
an obtaining step of using an obtaining device to obtain image data captured by detecting radial rays via a grid disposed in front of a radiation detector while resetting odd-numbered lines or even-numbered lines of the radiation detector;
a calculating step of calculating data lack information of the image data including grid components caused by the grid from a start of a radial rays to detection of the radial rays by the obtaining device, by calculating ratios of pixels in which data lack occurs in odd-numbered lines or even-numbered lines to pixels in which data lack does not occur using adjacent lines that are normal, wherein the data lack occurs in odd-numbered lines or even-numbered lines by resetting the odd-numbered lines or the even-numbered lines of the radiation detector;
a fitting step of fitting a model function representing data lack to the data lack information; and
a correcting step of correcting the image data using data lack information obtained by reducing grid components in accordance with the model function subjected to the fitting performed in the fitting step.

* * * * *